United States Patent [19]

Banks et al.

[11] Patent Number: 5,045,457
[45] Date of Patent: Sep. 3, 1991

[54] NOVEL COMPOUNDS

[75] Inventors: Rhona M. Banks; Simon E. Blanchflower; Peter R. Shelley, all of Surrey, England

[73] Assignee: Beecham Group p.l.c. of Beecham House, Middlesex, England

[21] Appl. No.: 299,933

[22] Filed: Jan. 23, 1989

[30] Foreign Application Priority Data

Jan. 22, 1988 [GB] United Kingdom ............... 8801488
Oct. 21, 1988 [GB] United Kingdom ............... 8824762
Nov. 1, 1988 [GB] United Kingdom ............... 8825561

[51] Int. Cl.$^5$ .................. C12N 1/20; C12P 19/62; C12P 17/08
[52] U.S. Cl. ..................... 435/124; 435/76; 435/253.5
[58] Field of Search ............... 435/124, 76, 253.5

[56] References Cited

U.S. PATENT DOCUMENTS 4,093,629  6/1978  Fisher ................... 548/407
4,134,973  1/1979  Fisher et al. ........... 536/7.1
4,144,352  3/1979  Putter .................. 514/450
4,789,684 12/1988  Goegelman .............. 514/450

Primary Examiner—Johnnie R. Brown
Assistant Examiner—Pamela S. Webber

Attorney, Agent, or Firm—Hopgood, Calimafde, Kalil, Blaustein & Judlowe

[57] ABSTRACT

Compounds of formula (II):

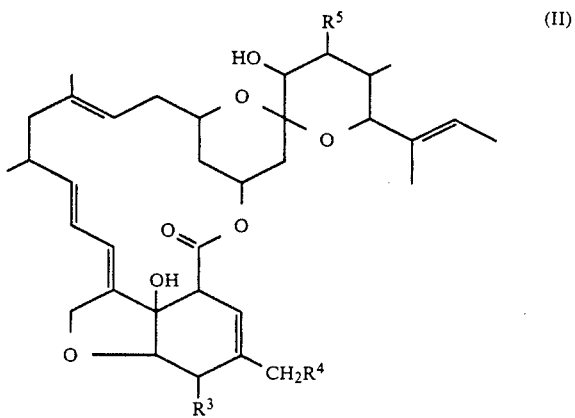

wherein $R^3$ is optionally protected hydroxy; one of $R^4$ and $R^5$ is optionally protected hydroxy; and the other of $R^4$ and $R^5$ is hydrogen, which are obtainable by the fermentation of a Streptomyces microorganism, have anthelmintic activity.

2 Claims, No Drawings

NOVEL COMPOUNDS

The present invention relates to novel anthelmintically active materials obtainable from a microorganism, to processes for their production, to pharmaceutical formulations containing them, and to their use in human or veterinary medicine.

A large number of microorganisms have been isolated, in particular from soil samples, and certain of those microorganisms have been found to produce various metabolites, which can be isolated and some of which have useful biological activity. One group of such metabolites is the milbemycins, which have been prepared by the cultivation of microorganisms of the genus Streptomyces and are described in inter alia GB-A-1,390,336, J. Antibiotics 29(3), 76-14 to 76-16 and 29 (6), 76-35 to 76-42, U.S. Pat. No. 4,144,352, and GB-A-2 056 986.

The α series of milbemycins include compounds of formula A:

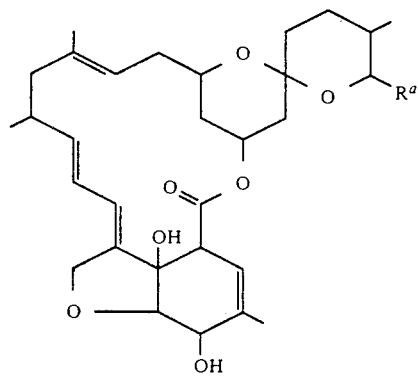

wherein $R^a$ is methyl, ethyl or isopropyl. In U.S. Pat. No. 4,144,352 it was disclosed that these and related compounds have anthelmintic activity.

Various milbemycin derivatives are disclosed in U.S. Pat. No. 4,093,629 and U.S. Pat. No. 4,134,973.

EP-A-0 170 006 and GB-A-2 166 436 disclose six further compounds of formula B:

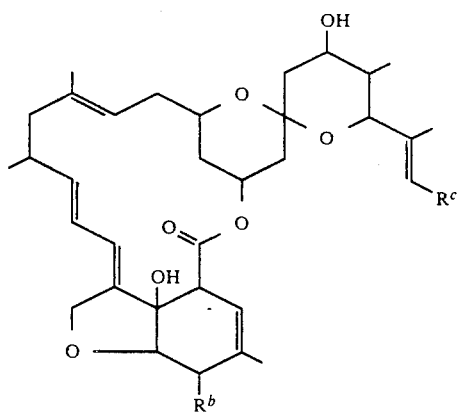

wherein $R^b$ is hydroxy or methoxy and $R^c$ is methyl, ethyl or isopropyl. These compounds were also prepared by the cultivation of Streptomyces microorganisms, and are stated to have anthelmintic activity.

We have now discovered a new group of compounds obtainable by the cultivation of a Streptomyces microorganism. These compounds have anthelmintic properties, and therefore are of use in the treatment of helminthiasis in humans and animals.

The present invention accordingly provides compounds of formula (I):

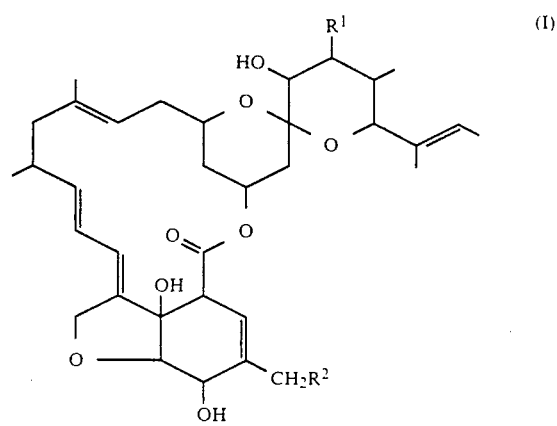

wherein $R^1$ and $R^2$ are as set out in Table I below:

TABLE I

| Compound | $R^1$ | $R^2$ |
|---|---|---|
| VM48130 | O—CO—CH(CH$_3$)$_2$ | H |
| VM48633 | H | O—CO—CH=C(CH$_3$)$_2$ |
| VM47704 | H | O—CO—CH$_2$—CH(CH$_3$)$_2$ |
| VM48642 | H | O—CO—CH$_2$—(furyl) |

Characterizing data for the compounds of the invention are set out hereinbelow in the Examples.

The absolute configuration of the compounds of the invention is believed to be as follows:

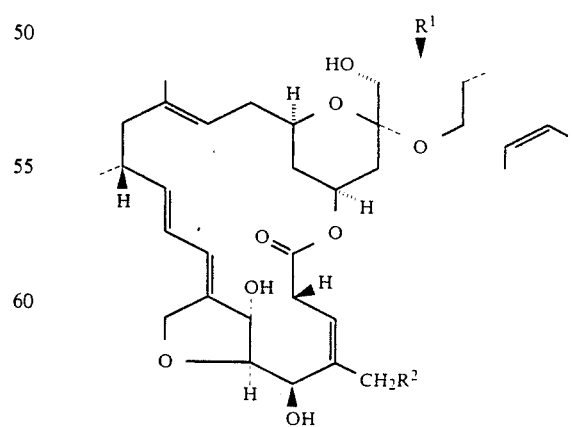

A broad aspect of the invention provides compounds of formula (II):

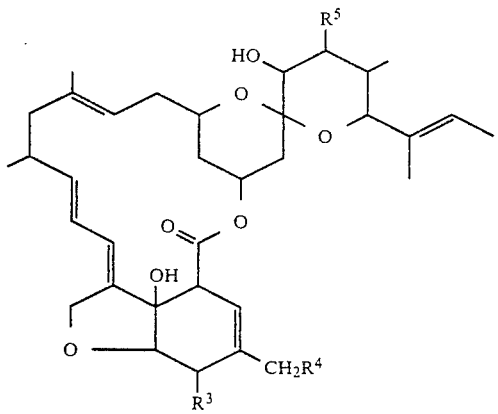
(II)

wherein $R^3$ is optionally protected hydroxy; one of $R^4$ and $R^5$ is optionally protected hydroxy; and the other of $R^4$ and $R^5$ is hydrogen.

Suitable protecting groups for hydroxy include acyl, such as those acyl groups listed in Table I. Other suitable groups, and methods for protecting and deprotecting hydroxy, are described in, for example, "Protective Groups in Organic Synthesis" Theodora W. Greene, Wiley-Interscience 1981 Ch 2, 10-86.

The present invention also provides a process for the production of a compound of the invention or a derivative thereof, which comprises cultivating a producing microorganism, and subsequently isolating the compound or derivative thereof from the culture.

The present invention furthermore provides a process for the preparation of a compound of the invention or derivative thereof, which comprises chromatographically separating the compound or derivative thereof from a solution thereof in admixture with other substances into a fraction comprising the compound or derivative thereof and other fractions.

The term 'cultivation' (and derivatives of that term) as used herein means the deliberate aerobic growth of an organism in the presence of assimilable sources of carbon, nitrogen, sulphur and mineral salts. Such aerobic growth may take place in a solid or semi-solid nutritive medium, or in a liquid medium in which the nutrients are dissolved or suspended. The cultivation may take place on an aerobic surface or by submerged culture. The nutritive medium may be composed of complex nutrients or may be chemically defined.

It has been found that suitable microorganisms for use in the cultivation process according to the invention include bacterial strains belonging to the genus Streptomyces that are capable of elaborating compounds according to the invention. It has further been found that examples of such strains include Streptomyces E225, which has been isolated from soil, and also mutants and natural variants thereof such as Streptomyces E225B.

The term 'mutant' as used herein includes any mutant strain which arises spontaneously or through the effect of an external agent whether that agent is applied deliberately or otherwise. Suitable methods of producing mutant strains include those outlined by H. I. Adler in 'Techniques for the Development of Microorganisms' in "Radiation and Radioisotopes for Industrial Microorganisms", Proceedings of a Symposium, Vienna, 1973, page 241, International Atomic Energy Authority, and these include:

(i) Ionizing radiation (e.g. X-rays and Y-rays), u.v. light, u.v. light plus a photosensitizing agent (e.g. 8-methoxypsoralen), nitrous acid, hydroxylamine, pyrimidine base analogues (e.g. 5-bromouracil), acridines, alkylating agents (e.g. mustard gas, ethylmethane sulphonate), hydrogen peroxide, phenols, formaldehyde, nitrosoguanidine, heat, and (ii) Genetic techniques, including, for example, recombination, transformation, transduction, lysogenisation, lysogenic conversion, protoplast fusion, and selective techniques for spontaneous mutants.

Streptomyces E225 and Streptomyces E225B are described EP-A-O 254 583 and U.S. Ser. No. 076,274. They have been deposited in the National Collection of Industrial and Marine Bacteria, Aberdeen, Scotland, the deposits (NCIB 12310 and 12509; filing dates 23rd July, 1986 and 20th July, 1987) being made under the terms of the Budapest Treaty on the International Recognition of the Deposit of Micro-organisms for the Purposes of Patent Procedure.

The characteristics of Streptomyces E225 were as follows:

After being grown on starch casein agar medium for 7 to 14 days at 27° C., Streptomyces E225 had produced a yellow-brown vegetative mycelium in which the hyphae did not fragment into coccoid or bacillary elements, and a yellow or white aerial mycelium which turned grey as the culture aged. The culture also produced a yellow soluble pigment and some colonies were observed to exude yellow droplets. The sporophores were arranged singly or in pairs along straight or flexuous main aerial hyphae, with no evidence of true verticillate branching, and terminated in spirals of 4 to 6 turns. Some sporophores presented a warty appearance, whilst older cultures developed moist black areas where spores had massed together.

Streptomyces E225 was non-sporulating on a yeast-malt agar medium.

The fermentation medium for cultivating the producing organism suitably contains sources of assimilable carbon and assimilable nitrogen together with inorganic salts. Suitable sources of nitrogen include yeast extract, soybean flour, meat extract, cottonseed flour, malt, distillers dried solubles, amino acids, protein hydrolysates and ammonium and nitrate nitrogen. Suitable carbon sources include glucose, lactose, maltose, starch and glycerol. Suitably the culture medium also includes alkali metal ions (for example, sodium), alkaline earth metal ions (for example, calcium and magnesium), halogen ions (for example, chloride), and trace elements (for example, iron, zinc, copper, manganese and cobalt).

The cultivation may suitably be effected at a temperature of about 20° to 35° C., advantageously 27° to 28° C., and the culture may suitably be harvested after 2 to 35 days, advantageously about 5 to 20 days, after the initiation of fermentation in order to given an optimum yield of the desired compound of the invention.

The desired compound or derivative thereof may then be isolated from the culture medium and worked up and purified using conventional techniques.

The desired product may be obtained from either the mycelial growth or from the culture filtrate. It may therefore be convenient for the first isolation step to involve the separation of solid material from the fermentation broth by, for example, filtration or centrifugation, to give a clarified culture filtrate and solid material. Alternatively, the fermentation broth can be extracted directly.

It may be convenient to include an organic solvent extraction step in the isolation or purification procedure, suitably using a solvent such as butanol or toluene.

Further isolation of the desired compound may conveniently be effected by chromatographic techniques. The extract may contain additional substances, and therefore chromatographic separation may result in a plurality of fractions, of which the desired fraction or fractions is or are the fraction(s) comprising the desired compound or a derivative thereof.

The desired fraction(s) may readily be identified in a routine manner by testing for anthelmintic activity and/or by monitoring each fraction chromatographically. The desired fraction(s) is/are that/those identified by such procedures as containing the desired compound or a derivative thereof.

If necessary, repeated chromatographic separation may be carried out in a routine manner. At each stage of the separation procedure, the fractions containing the desired compound or a derivative thereof may be combined and then subjected to further purification steps. In the initial separation steps, it may be convenient to identify the desired fractions merely as those having anthelmintic activity and to combine all such fractions. In later stages of the separation, it may be necessary to identify the desired fraction or fractions more precisely in order to separate the desired compound or a derivative thereof from any other substances that may be present. Separation may advantageously be continued in order to give one or more fractions consisting essentially of the desired compound or a derivative thereof.

The expression 'fraction consisting essentially of the desired compound or a derivative thereof' means a fraction containing the desired compound or a derivative thereof as the sole component present in that fraction, or as the major component (whether other components are active or are inactive impurities) present in that fraction. The expression 'major component' means the component that is present in the greatest amount relative to other individual components (exclusive of solvent). Suitably, the major component is present in an amount greater than the sum of the amounts of all other components (excluding solvent). More suitably, the major component is present in an amount of at least 60%, advantageously at least 70%, preferably at least 80%, especially from 90% to 100%, by weight, relative to the total amount of active material, or relative to the total amount of material whether active or inactive (exclusive of solvent), as the case may be, present in the fraction. Typically, the compounds of the invention are produced in admixture with one another, so that fractions may be obtained which consist essentially of a mixture of two or more compounds of the invention.

It has been found convenient to carry out chromatographic separation on silica gel (using, for example, a silica 60 column). Two or more chromatographic separation steps may be carried out successively. Elution of the chromatographic columns may conveniently be effected using organic solvents, either alone or in admixture with one another, e.g. hexane/acetone, diethylether/petroleum ether, or methanol/chloroform.

The compound or mixture of compounds according to the invention is suitably provided in substantially pure form, for example at least 50% pure, suitably at least 60% pure, advantageously at least 75% pure, preferably at least 85% pure, more preferably at least 95% pure, especially at least 98% pure, all percentages being calculated as weight/weight. An impure or less pure form of a compound according to the invention may, for example, be used in the preparation of a more pure form of the same compound or of a related compound (for example a corresponding derivative) suitable for pharmaceutical use.

The compounds of the invention have parasiticidal properties, for example against nematodes such as *Trichostronqylus colubriformis*, and are useful for the treatment of helminthiasis in animals such as mammals, including humans and domesticated animals (including farm animals).

Accordingly the present invention also provides a compound according to the invention, for use in the treatment of the human or animal body, especially for treating endo- and ectoparasitic infestations and particularly for treating helminthiasis of domestic and farm animals.

The term helminthiasis encompasses those diseases of man and animals caused by infestation with parasitic worms such as Strongyles, Ascarids, hookworms lungworms, filarial worms and whipworms. The compound may also be used against nematodes occurring in the soil or parasitic to plants.

The compounds of the invention are also active against Arthropods. The phylum Arthropoda comprises insects—such as biting flies, lice, bugs, beetles and fleas—and arachnids–such as mites and ticks.

Thus, a broad aspect of the invention provides a method of eradicating arthropod or nematode infestations, which method comprises applying a compound according to the invention or a derivative thereof to the arthropods or nematodes or to their environment.

The present invention thus provides a pesticidal composition comprising a compound according to the invention or a derivative thereof together with a suitable carrier or excipient, such as an aerosol formulation.

The present invention also provides a pharmaceutical or veterinary composition comprising a compound according to the invention or a pharmaceutically acceptable derivative thereof together with a pharmaceutically or veterinarily acceptable carrier or excipient.

The present invention also provides a method of treatment or prophylaxis of endo- and ectoparasitic infestations, especially helminthiasis, of animals, especially humans and domesticated mammals, which comprises administering an effective non-toxic amount of a compound according to the invention or a pharmaceutically acceptable derivative thereof, or a composition according to the invention, to a patient in need thereof.

The composition according to the invention may be formulated for administration in any convenient way for use in human or veterinary medicine, by analogy with other anthelmintics.

In suitable formulations the drug may be administered to animals orally (as a paste, drench, bolus, capsule or tablet), parenterally, percutaneously, as a food additive (e.g. granules, pellets or powder), or may be prepared as an aerosol spray formulation.

The compounds of the invention may be formulated as a mixture with each other and/or with other anthelmintics, insecticides, acaricides or other pharmacologically active substances.

Suitably the composition consists of sufficient material to provide a dose of from 0.01 to 100mg of active ingredient per kg of animal body weight per dose, more suitably 1.0 to 100mg/kg per dose.

A composition according to the invention may suitably contain from 0.1% by weight, preferably from 1.0 to 60% by weight, of the compound according to the invention (based on the total weight of the composition), depending on the method of administration.

In certain circumstances the crude fermentation broth may be administered, for example by incorporating the freeze-dried fermentation broth into the feed of the animal.

It will be appreciated that, in some cases, it will be advisable to repeat the dosing of the infected or potentially infected human or animal with the compound of the invention according to conventional dosage regimes used with anthelmintics.

The following Examples illustrate the invention.

EXAMPLE 1

CULTURE

Streptomyces sp. NCIB 12509 was maintained as vegetative mycelium stored in liquid nitrogen.

1ST STAGE SEED 100 mls Medium Y was sterilized in 500 ml Erlenmeyer flasks closed with cotton gauze caps.

| Medium Y contained:- | |
|---|---|
| *Special Peptone | 0.25% |
| *Lab Lemco | 0.25% |
| *Tryptone | 0.25% |
| *Neutralised Soya Peptone | 0.25% |
| *Malt Extract | 0.25% |
| Soluble Starch | 0.25% |
| Glucose monohydrate | 0.25% |
| Glycerol | 0.25% |
| ɸTrace elements solution | 10 ml/litre |
| pH was unadjusted | |
| ɸThe trace elements solution contained:- | |
| $CaCl_2.2H_2O$ | 1.0% |
| $MgCl_2.6H_2O$ | 1.0% |
| NaCl | 1.0% |
| $FeCl_3$ | 0.3% |
| $ZnCl_2$ | 0.05% |
| $CuCl_2.2H_2O$ | 0.05% |
| $MnSO_4.4H_2O$ | 0.05% |
| $CoCl_2.6H_2O$ | 0.05% |

(*These products were supplied by Oxoid Ltd., Basingstoke, Hants. UK)

One flask of Medium Y was inoculated with the contents (1.5 ml) of one ampoule of preserved culture. The flask was incubated at 25° C. on a gyratory shaker at 240 rpm for 48 hours.

2ND STAGE SEED

Seed Medium C was sterilized in 100 ml amounts in 500ml Erlenmeyer flasks closed with cotton gauze caps.

| Medium C contained: | |
|---|---|
| Arkasoy 50 | 1.0% |
| Glucose monohydrate | 2.0% |
| Spray dried Corn Steep Liquor | 0.5% |
| NaCl | 0.3% |
| pH adjusted to 6.8. | |

(Arkasoy 50 was supplied by British Arkady Co. Manchester, UK).
(Corn Steep Liquor was supplied by Roquette UK Ltd., Tunbridge Wells, Kent, UK).

Flasks of medium C were inoculated with 4% of the 1st stage seed inoculum. These were incubated a 26° C. on a gyratory shaker at 240rpm for 72 hours.

3RD STAGE SEED 15 liters of Medium C together with Polypropylene glycol (P2000) 0.1% v/v were sterilized in a 20 liter Biolafitte fermenter (Biolafitte, Poissey, France). The fermenter was fully baffled and fitted with three vaned-disc impellers. Sterile air was supplied at 1 v.v.m. and agitation was at 200rpm.

The contents of two second-stage seed flasks were used to inoculate one 20 liter fermenter and incubation, at 26° C., was for 48 hours.

4TH STAGE SEED 100 liters Medium C was sterilized at 121° C. in a 150 liter Braun fermenter (B. Braun, Melsungen, W. Germany). 0.1% Antifoaming agent was included with the medium and consisted of 10% pluronic L81 in soybean oil. (Pluronic L81 was supplied by Blagden-Campbell Chemical Co., Croydon, UK).

The fermenter was fully baffled and fitted with three vaned-disc impellers. Agitation was at 120rpm and sterile air supplied at 1 v.v.m. The fermenter was inoculated with 4 liter of the 3rd stage seed and incubated at 28° C. for 48 hours.

FERMENTATION STAGE 3000 liters of Medium F1 was sterilized in a 4500 liter Bioengineering fermenter (Bioengineering-Wald, Switzerland).

| Medium F1 contained:- | |
|---|---|
| Arkasoy 50 | 1.0% |
| Glucose monohydrate | 2.0% |
| Dextrin 07005 | 2.0% |
| Casein | 0.2% |
| $MgSO_4$ | 0.1% |
| $CaCO_3$ | 0.5% |
| 10% Pluronic L81 in soybean oil | 0.1% |

(Dextrin 07005 was supplied by Corn Products Ltd., Manchester, UK)
(Casein was supplied by Oxoid Ltd. Hants., UK).
pH adjusted to 6.0

The fermenter was fully baffled and fitted with three, vaned-disc impellers. Sterile air was supplied at 0.5 v.v.m.

The fermenter was inoculated with 100 liters of fourth stage seed inoculum and incubated at 26° C. The agitation rate was maintained at the following rates:

| 0-2 days | 50 rpm |
|---|---|
| 2-3 days | 75 rpm |
| 3 days-harvest | 100 rpm |

The fermentation ran for 17 days and extra shots of antifoaming agent were added on demand.

ISOLATION PROCEDURE

At harvest whole broth was transferred to a separate stirred vessel and 10% v/v butan-1-ol was added. The mixture was stirred for 16 hours at 7° C. Thereafter the whole broth (2339 liters) was fed at 5 liters/minute, together with butan-1-ol at 1.7 liters/minute through an in-line static mixer to a Westfalia SA7-03-076 liquid/-liquid/solid centrifugal separator (Westfalia Separator Ltd., Oelde, W. Germany). The accumulated solids were discharged intermittently as required.

The raffinate and mycelial solids were combined and submitted to a second, similar extraction with butan-1-ol. Combined butanol extracts were concentrated in vacuo to 20 liters. 40 liters petroleum spirit (60°–80° C.) was added to precipitate pigmented impurities which were removed by centrifugation. The supernatant was concentrated in vacuo to 15 liters.

CHROMATOGRAPHIC PURIFICATION

The concentrate was chromatographed on a column (600mm diameter×200mm) of silica gel (Riedel de Haen, Seelze, W. Germany, 32-63 μm), eluting with a step gradient of ethyl acetate in petroleum spirit (60°-80° C.). Fractions obtained using >8% ethyl acetate, containing VM 47704 and other active material were set aside. All of the remaining milbemycin - containing fractions were rechromatographed on a similar column, resulting in the separation of a further quantity of VM 47704 and other active material which was combined with that already obtained and evaporated to an oily concentrate (208g).

This was again chromatographed on silica gel (150mm×180mm column), eluting with a step gradient f ethyl acetate in petroleum spirit (60°-80o), using 3.3 liters pure petroleum spirit, followed by 6. liters each of 15%, 25%, 30%, 35% and 40% v/v ethyl acetate in petroleum spirit. The first 25 liters of eluate was discarded, thereafter fractions of 2 liters were collected. Fractions 3-8 were combined an concentrated to an oil.

This material was chromatographed on a column (75mm diameter×500mm) of Sephadex® LH 20 (Pharmacia, Milton Keynes, UK) using methanol as eluant. All fractions containing milbemycin components were combined.

Further purification was achieved using chromatography on reverse-phase silica. Matrex® $C_{18}$ silica, 20-45 μm, 60A pore size (Amicon, Stonehouse, UK) was used for all subsequent columns. Product obtained from the Sephadex® LH 20 column was chromatographed on a 100mm diameter×180 mm column of $C_{18}$ silica, eluting with 85% methanol. The first 1 liter of eluant was discarded, thereafter 20×100 ml fractions, all containing milbemycin components were collected and combined.

The solution so obtained was chromatographed on a similar column, eluting firstly with 85% metanol, then with 87.5% methanol. After discarding the first 1 liter of eluate, 36 fractions each of 85 ml, containing active material other than VM 47704 were collected.

Thereafter elution was with 87.5% methanol which eluted VM 47704 admixed with other active material.

The latter fractions were chromatographed on a 100mm diameter×260mm column (designated 22I), eluting with 85% methanol. 100 ml fractions were collected. Enrichment of VM 47704 was observed in fractions 42-55. Fractions 35-41 contained additional product.

Fractions 42-55 from column 22I were chromatographed on a similar column (designated 22J), eluting with 82.5% methanol. The first 7.2 liters was discarded then 100 ml fractions were collected. The majority of the VM 47704 was found in fractions 66-85 and further, less pure, product was present in fractions 57-65.

The less pure fractions from columns 22I and 22J were combined and chromatographed on a column (80mm diameter ×600mm) using 81% methanol as eluant. The first 9.3 liters were discarded, then 100 ml fractions were collected. Fractions 76-86 containing predominantly VM 47704 were combined with fractions 66-85 from column 22J and chromatographed on the same column, using 79% methanol as eluant. The first 20 liters were discarded then 100 ml fractions were collected. Fractions 34-55 were evaporated to dryness to give 209 mg VM 47704.

Characterization Data for VM

Mass (Electron Impact Mass Spectroscopy) $[M]+ = 684$; $\delta 13_C$ (CDl$_3$) 173.0, 172.9, 142.9, 139.1, 137.1, 136.4, 134.0, 123.6, 123.3, 121.7, 120.54, 120.47, 98.8, 81.9, 80.3, 79.0, 71.5, 68.8, 68.4, 67.9, 64.6, 64.1, 48.4, 45.5, 43.2, 36.8, 36.4, 36.3, 35.9, 34.6, 32.0, 25.6, 22.4, 22.2, 17.4, 15.5, 13.1, 10.9.

EXAMPLES 2 AND 3

The seed stages and fermentation stages were carried out as in Example 1, except that in the fermentation stage the agitation was maintained at the following rates:

| 0-3 days | 50 rpm |
| --- | --- |
| 3 days-harvest | 100 rpm |

The fermentation broth was harvested after 404 hours. Whole broth was discharged from the fermenter and saturated with butanol. Product was extracted with ⅓ volume butanol using an in-line static mixer followed by the Westfalia liquid/liquid/solid separator. The broth was processed at 5 1/min resulting in ca 80% yield. A second, similar, extraction was performed to give essentially quantitative recovery.

Combined butanol extracts were combined, concentrated to low volume (19 1) and 2 volumes of petroleum spirit (60-80° ) were added to precipitate pigmented impurities. Reconcentration resulted in 10.8 1 brown oil which was chromatographed on 28 kg silica gel packed in a 600 mm diameter column. Elution was carried out using increasing concentrations of ethyl acetate (up to 50%) in petrol.

Fractions containing VM 48130 and VM 48633 were identified and subjected to further chromatography. VM 48130 (Example 2) and VM 48633 (Example 3)

A 1.8 g fraction containing VM 48130 and VM 48633 was subjected to preparative reverse phase HPLC using a Dynamax-60A C-18 column (500×21.4mm, Rainin Instrument Company, USA), eluted with a methanol:water gradient at 10ml/min (82:18 methanol:water rising to 100% methanol over 140 min), monitored by UV spectroscopy at 244 nm. VM 48130 and VM 48633 were detected in the same fractions which were pooled and the solvent evaporated to yield 97.4 mg of material. This was further purified by preparative silica HPLC using a Dynamax-60A Si column (250×21.4mm, Rainin Instrument Company, USA), eluted with a hexane:acetone gradient (87:13 to 82:18 over 120 min at 10 ml/min). Fractions were collected and identified by TLC (silica gel plates run with 60:40 hexane:acetone).

This produced substantially pure VM 48633 (4.9mg; $\lambda_{max}$ (CH$_3$OH) 244nm, mass (FAB Na$^+$/NOBA) $[MNa]+ = 705$, $\delta 13_c$(CDCl$_3$) 173.2, 166.4, 157.8, 142.9, 139.2, 137.2, 136.8. 134.1. 123.7. 123 4, 121.4, 120.6, 120.5, 115.6, 98.9. 81.9. 80.3. 79.1. 71.6, 68.8. 68.5. 68.0, 64.7, 63.5. 48.5. 45.6. 36.9. 36.45, 36.37. 36.0, 34.6, 32.1, 27.5. 22.3. 20.3. 17.5. 15.5. 13.1, 10.9 ppm.

Fractions containing VM 48130 (10.6mg) required final purification by semipreparative HPLC (Hypersil 5 μm ODS 250×10 mm column, HPLC Technology Ltd), eluted with a methanol:water gradient (77:23 methanol:water, rising to 85.15 over 60 min, flow 3 ml/min), monitored by UV spectroscopy at 244nm. This yielded 4.1 mg of substantially pure VM 48130;$\lambda_{max}$ (CH$_3$OH) 244nm, mass (FAB, Na$^+$/NOBA) $[MNa]+ = 693$; $\delta 13_c$ (CDCl$_3$) 177.8, 173.7, 142.8, 139.5, 137.9, 137.4, 133.1, 124.9, 123.4, 120.4, 120.3, 118.1, 100.2, 80.2, 79.2, 76.0, 75.4, 68.5, 68.1, 67.7, 48.5, 45.7, 37.7, 36.21, 36.14, 36.0, 34.6, 34.3, 22.3, 19.9, 19.2, 19.0, 15.6, 13.2, 13.0, 10.8 ppm.

They have retention times of 12.3 min (VM 48130) and 12.9 (VM 48633) when subjected to HPLC under the following conditions: Ultrasphere ODS 5%m column 250×4.6 mm (Altex) eluted with methanol:water (85.15) at a flow rate of 1 ml/min and monitored by UV spectroscopy at 244 nm.

EXAMPLE 4

The seed stages and fermentation stages were carried out essentially as in Example 1.

Whole broth (3m$^3$) was mixed with toluene (1m$^3$), adjusted to pH 2.5 using 25% $H_2SO_4$, then heated to 75° C. and held at this temperature for 1 hour. After cooling to 30° C., the mixture was passed through a model SA7 separator (Westfalia Separator Ltd., Habig House, Old Wolverton, Milton Keynes, UK) to obtain a particulate-free toluene extract. 1% w/v aqueous sodium hydrogen carbonate solution (250 dm$^3$) was added and the mixture stirred with the intention of extracting acidic impurities. However an intractable emulsion was produced which required treatment at pH 3 and 60° C. before phase separation was possible. The aqueous phase was discarded.

1% w/v activated carbon (Norit GSX, Norit (UK) Ltd., Cambuslang Industrial Estate, Glasgow) was added to the toluene solution and the mixture was stirred for 50 minutes. 1% w/v filter aid (Dicalite 478, Dicalite Europe Nord, Ghent, Belgium) was added and the mixture filtered under vacuum. The filtrate was concentrated under reduced pressure to 11 dm$^3$ then petroleum spirit (60°-80°, 44 dm$^3$) was added. A clear solution was decanted from the precipitated solid and concentrated in vacuo to give a yellow-brown oil (6.47 kg).

This material was loaded on to a chromatographic column mm diameter, 180 mm high containing 28 kg silica gel (Kieselgel S, 32-63 m, Riedel de Haen, Seeize, West Germany) packed in petroleum spirit 60°-80° C. Elution was performed using a step gradient of ethyl acetate in petroleum spirit using the following volumes:

| ethyl acetate | volume dm$^3$ |
| --- | --- |
| 0 | 30 |
| 4 | 120 |
| 8 | 120 |
| 12 | 240 |
| 16 | 240 |
| 20 | 240 |
| 25 | 240 |
| 30 | 240 |
| 50 | 200 |

The latter part of the 30% ethyl acetate eluate and the ethyl acetate eluate were combined and concentrated to an oil (149 g) which was dissolved in 80% methanol at 50° C. then chromatographed at ambient temperature on octadecyl silica (Matrex $C_{18}$ silica, 20-45 μm, 6 nm pore size, Amicon, Stonehouse, Gloucestershire, UK).

The column was 100 mm diameter, packed to a depth of 200 mm and was eluted with 80% v/v methanol. Initial eluate (860 cm$^3$) was discarded; thereafter 86×90 cm$^3$ fractions were collected. Fractions 41-86 were combined and concentrated to an oil (22.6 g). This was chromatographed under similar conditions, discarding the initial eluate (600 cm$^3$) then collecting 160×90 cm$^3$ fractions. Fractions 112-135 were combined and concentrated to an oil (product A, 5 g). Fractions 109-111 together with fractions 136-151 were combined and concentrated to an oil (product B, 3.5g).

Product A was chromatographed on octadecyl silica (80 mm diameter×600 mm) using 80% v/v methanol. Initial eluate (7.7 dm3) was discarded. Thereafter 85×90 cm$^3$ fractions were collected. Fractions 60-75 were combined and evaporated to dryness (600 mg). Product B was chromatographed on a similar column using 77.5% v/v methanol as eluant. Initial eluate (15.75 dm$^3$) was discarded. Thereafter 106×90 cm$^3$ fractions were collected. Fractions 45-61 were combined and evaporated to dryness (166 mg).

The purified products A and B detailed above were combined (766 mg) and chromatographed on another similar column using 76.3% methanol as eluant. Initial eluate (20 dm$^3$) was discarded. Thereafter 113×90 cm$^3$ fractions were collected. Fractions 45-76 were combined and evaporated to dryness (380 mg).

This material was further chromatographed by preparative HPLC using a Dynamax 60 - A Silica column (21.4×250 mm. Rainin Instrument Co., USA) eluted with a Hexane: Acetone gradient (87:13 Hexane: Acetone changing to 82:18 over 120 min and thereafter holding at 82:18) pumped at 10 mls/min. 10 ml fractions were collected throughout and examined by analytical TLC (Silica plates eluted with 60:40 Hexane: Acetone). Fractions 95-162 from this column were pooled and the solvent evaporated to yield 128.7 mg of impure material.

This material was purified by two runs of preparative reverse phase HPLC (Dynamax - 60A C-18 21.4×250 mm, Rainin Instrument Co., USA) utilizing Acetonitrile: Water as mobile phase at 1 ml/min. collecting 1 ml fractions throughout and monitoring by uv absorbance (244 mm).

The initial run employed 75:25 Acetonitrile water and the material of interest was rapidly eluted, being found in fractions 3-20, this was dried, dissolved in Acetonitrile, filtered and re-chromatographed using 65 : 35 Acetonitrile: water. VM 48642 was eluted in fractions 42-50 which were pooled and dried to yield 12.2 mg.

Characterization Data VM 48642

FAB mass spectrometry indicated a molecular weight of 708. $13_C$(CDCl$_3$) 173.1, 170.9, 143.08, 143.05, 140.5, 139.1, 137.2, 136.2, 134.1, 123.7, 123.3, 122.1, 120.59, 120.57, 117.1, 111.3, 98.9, 81.9, 80.3, 79.0, 71.6, 68.9, 68.5, 68.0, 64.8, 64.7, 48.5, 45.5, 36.8, 36.43, 36.37, 36.0, 34.6, 32.1, 30.8, 22.3, 17.5, 15.5, 13.1, 10.9. ppm.

It has the following retention time when examined by reverse phase HPLC (Rainin Instrument Co., USA, Microsorb C - 18 4.6×250 mm column) eluted with methanol: water 85:15 at 1 ml/min and monitored by uv spectroscopy at 244 nm: 12.78 minutes

EXAMPLE 5

Biological Activity

Four-week-old Mongolian gerbils of mixed sex were each infected with 750 *Trichostronqylus colubriformis* infective larvae (sheep strain) by gavage. Twenty eight days after infection these animals were randomly allocated into groups. On the same day worm egg counts were carried out on pooled faecal samples from each group to confirm that the infections had established and determine the pre-dose egg count.

At 29 days post-infection, different groups of animals were treated with VM 48130, VM 48633 and VM 47704 at 1 mg/kg and 0.1 mg/kg. All treatments were administered orally by gavage. Test compounds were dissolved in 0.2 ml methanol and diluted to a concentration of 1 mg/ml in water containing 0.05% Tween 20. A further 1/10 dilution, made in water containing 0.05% Tween 20, was prepared (i.e. 0.1 mg/ml) and used to dose the animals.

Three and four days after treatment worm egg counts were carried out on pooled faecal samples from each group to determine the effect of treatment. Anthelmintic activity was expressed thus:

$$\% \text{ reduction in egg count} = 100 - \left[ \frac{\text{mean post-treatment egg count}}{\text{pre-treatment egg count}} \times 100 \right]$$

The results are summarized in Table II.

TABLE II

| In vivo Activity Gerbil/Trichostrongylus Model | Reduction in Egg Count | | |
|---|---|---|---|
| | VM 48130 | VM 48633 | VM 47704 |
| Dose | | | |
| 1 mg/kg | 99 | 100 | 99 |
| 0.1 mg/kg | 7 | 75 | 18 |

We claim:

1. A process for the production of a compound having the formula:

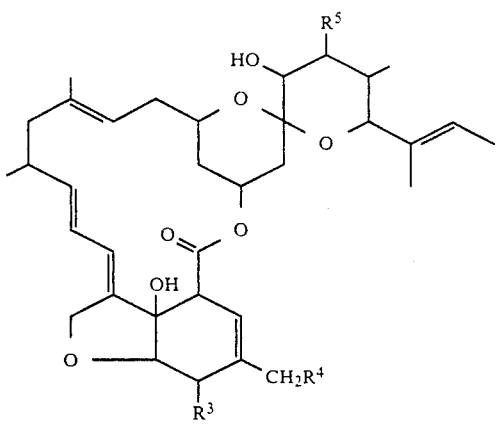

wherein $R^3$ is hydroxy optionally being protected; one of $R^4$ and $R^5$ is hydroxy optionally being protected; and the other of $R^4$ and $R^5$ is hydrogen, which process comprises cultivating a microorganism having all of the identifying characteristics of Streptomyces E225 NCIB 12310 and Streptomyces E225B NCIB 12509 or a mutant thereof.

2. A process according to claim 1, for the production of the compound according to claim 1 wherein (a) $R^3$ is hydroxy, $R^4$ is hydrogen and $R^5$ is 2-methyl-propanoyloxy, or (b) $R^3$ is hydroxy, $R^4$ is 3-methyl-but-2-enoyloxy, 3-methyl-butanoyloxy, or 2-furan-3yl-acetyloxy, and $R^5$ is hydrogen, wherein the compound is produced directly by the microorganisms of claim 1.

* * * * *